(12) United States Patent
Hanley

(10) Patent No.: US 7,501,290 B2
(45) Date of Patent: Mar. 10, 2009

(54) INTRAPLEXING METHOD FOR IMPROVING PRECISION OF SUSPENDED MICROARRAY ASSAYS

(76) Inventor: Brian P. Hanley, 300 Atrium Way #312, Davis, CA (US) 95616

( * ) Notice: Subject to any disclaimer, the term of this patent is extended or adjusted under 35 U.S.C. 154(b) by 2 days.

(21) Appl. No.: 11/901,117

(22) Filed: Sep. 13, 2007

(65) Prior Publication Data

US 2008/0064122 A1 Mar. 13, 2008

Related U.S. Application Data

(60) Provisional application No. 60/844,577, filed on Sep. 13, 2006.

(51) Int. Cl.
*G01N 33/543* (2006.01)
(52) U.S. Cl. .................................... 436/518
(58) Field of Classification Search ................ 436/518, 436/523; 435/7.92
See application file for complete search history.

(56) References Cited

U.S. PATENT DOCUMENTS

| | | | |
|---|---|---|---|
| 6,051,377 | A | 4/2000 | Mandecki |
| 6,268,222 | B1 | 7/2001 | Chandler et al. |
| 6,361,950 | B1 | 3/2002 | Mandecki |
| 6,376,187 | B1 | 4/2002 | Mandecki |
| 6,696,265 | B1 | 2/2004 | Spain |
| 6,916,661 | B2 | 7/2005 | Chandler et al. |
| 6,919,009 | B2 | 7/2005 | Stonas et al. |
| 6,939,720 | B2 | 9/2005 | Chandler et al. |
| 7,033,754 | B2 * | 4/2006 | Chee et al. ............. 435/6 |
| 7,045,049 | B1 | 5/2006 | Natan et al. |
| 7,141,431 | B2 | 11/2006 | Chandler et al. |
| 7,164,533 | B2 | 1/2007 | Moon et al. |

OTHER PUBLICATIONS

J. R. Kettman, T. Davies, D. Chandler, K. G. Oliver, R. J. Fulton, "Classification and properties of 64 multiplexed microsphere sets", Cytometry, Jan. 1999, vol. 33, Issue 2, pp. 234-243, Published by: Wiley Interscience, USA.

Kathryn L. Kellara and Marie A. Iannone, "Multiplexed microsphere-based flow cytometric assays", Experimental Hematology, Nov. 1, 2002, vol. 30, Issue 11, pp. 1227-1237, published by: Elsevier Science Inc., USA.

Hanley, Brian. "Variance in multiplex suspension array assays: carryover of microspheres between sample wells.", Journal of Negative Results in Biomedicine, Apr. 25, 2007, vol. 6, Issue 6, Online, published by: Biomed Central, London.

James W. Jacobson, Kerry G. Oliver, Christy Weiss, and John Kettman Analysis of Individual Data from Bead-Based Assays ("Bead Arrays") Cytometry Part A, Apr. 13, 2006, vol. 69A, pp. 384-390, Online, published by Wiley InterScience, http://www.interscience.wiley.com/.

Hanley, Brian "Variance in multiplex suspension array assays: intraplex method improves reliability.", Theoretical Biology and Medical Modelling, Aug. 29, 2007, vol. 4, Issue 32, Online, published by: Biomed Central, London.

Hanley, Brian "Variance in multiplex suspension array assays: microsphere size impact.", Theoretical Biology and Medical Modelling, Aug. 23, 2007, vol. 4, Issue 31, Online, published by: Biomed Central, London.

Wai-Ming Lee, Kris Grindle, Tressa Pappas, David Marshall, Michael Moser, Edward Beaty, Peter A Shult, James Prudent, and James E. Gern "A High-Throughput, Sensitive and Accurate Multiplex PCR-1 Microsphere Flow Cytometry System for Large-Scale Comprehensive Detection of Respiratory Viruses", J. Clin. Microbiol., May 30, 2007, Ahead of Print, Online, published by: American Society for Microbiology, Washington, D.C.

* cited by examiner

*Primary Examiner*—Ann Y Lam
(74) *Attorney, Agent, or Firm*—Temmerman Law Office; Mathew J. Temmerman

(57) ABSTRACT

A method for making suspended microarray readings from a single sample statistically significant in a reliable manner. It can be applied to any assay system that uses discrete particles where the particles are coupled with an assay. Most of these systems suspend the particles in fluid and read the assay result using flow cytometry. However, other methods such as the distribution of tiny assay devices coupled with miniature transponders, where the sampling is of the environment, can also make use of this method. This invention combines multiple separately identified assays of one sample, where the multiple assays are for a single analyte and sets of assays have differing sensitivity to said analyte. By elimination of outliers, averaging, and taking ratios of averages, this method makes possible highly reliable diagnostics. This method compensates for multiple stochastic and non-stochastic sources of errors that can occur in this type of assay system.

17 Claims, 5 Drawing Sheets

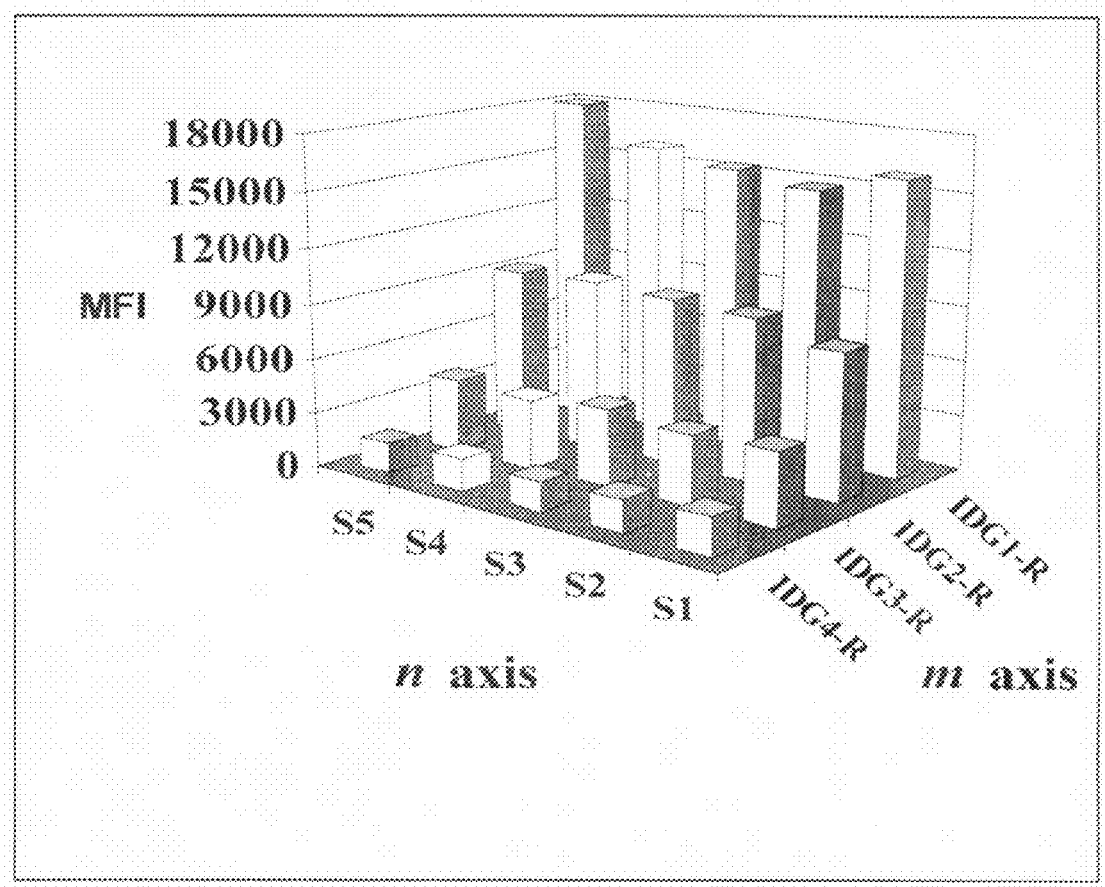
Fig. 3A
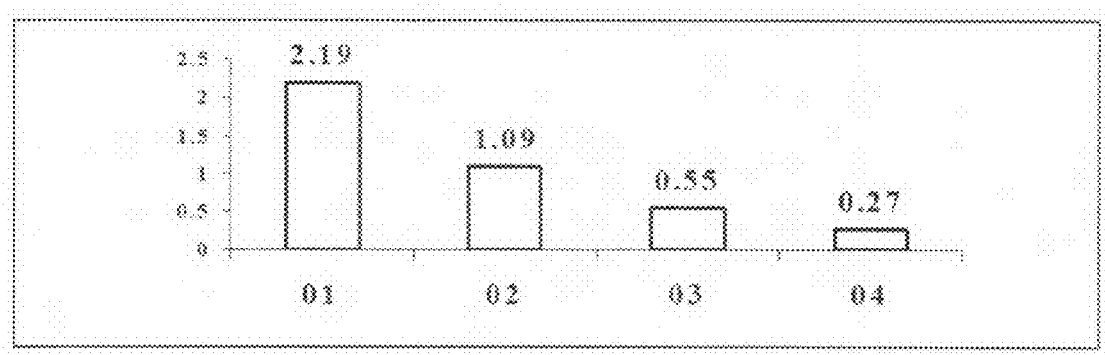
Fig. 3B
Fig. 3C

Fig. 5

INTRAPLEXING METHOD FOR IMPROVING PRECISION OF SUSPENDED MICROARRAY ASSAYS

RELATED APPLICATION

This application claims priority from the U.S. provisional application with Ser. No. 60/844,577, which was filed on Sep. 13, 2006. The disclosure of that provisional application is incorporated herein as if set out in full.

FIELD OF THE INVENTION

The present invention relates to assays, specifically to intraplexing methods for improving the precision of suspended microarray assays.

GENERAL BACKGROUND AND OBJECTS OF THE INVENTION

A number of patents exist for various forms of suspended microarray assays, including patents for substrate microparticles of various kinds, how their sets are differentiated, processing the array data and what is termed "multiplexing" of assays. A list of these references is submitted in an Information Disclosure Statement accompanying this application. A number of these patents are held by the Luminex® corporation, a company that produces specialized flow cytometers for use with microsphere based suspended microarray assays.

Of those patents that cover multiplexing, none discuss the intentional use of more than one particle set targeted at the same analyte within a sample. None discuss how one might make use of a multiplicity of sensitivities to the same analyte by a set of suspended microarray assays in order to better determine analyte concentration. None disclose using a multiplicity of assays that should have the same sensitivity to analyte to improve precision. Nor do any of the listed patents discuss how both techniques (multiple identically sensitive assays and multiple differentially sensitive assays for the same analyte) can be combined together to achieve an even higher level of precision and repeatability. None of the patents discuss how such intraplexed assays can be used to eliminate instrumentation variances and make accurate estimates of true concentration of analytes without necessarily requiring calibration standards be run with every multi-well assay that is performed.

To define intraplexing clearly, special terminology has been created because without it, experts became confused as to what exactly was being referred to. For this reason, a single particle (which is, for Luminex®, a microsphere) is called an SMP (suspended microarray particle.) A set of microspheres that are all labeled with the same classifier is called an SMPCS (suspended microarray particle category set). (Hence, SMPCSs is the plural form of SMPCS.) These two differentiations are all that is necessary for understanding suspended microarray systems. An SMPCS corresponds to what Luminex® commonly calls "a microbead region", a "microbead set" or more colloquially, "a microbead" and is usually interchangeable with "bead number", since Luminex® classifies their beads to users by numbers from 001 to 100. A method of classification of such sets will sometimes be referred to herein as a "classifier."

Intraplexing also introduces a superset, which is the "suspended microarray particle category set—identical group," or SMPCS-IDG. (Likewise SMPCS-IDGs is the plural form.) In an SMPCS-IDG, a set of differently numbered microparticle sets are all coated with the same reagent(s) so as to make them identical in sensitivity to the analyte being assayed. Bearing this introduction in mind, these terms are discussed in more detail below.

A suspended microarray system uses a population of suspended microarray particles (SMPs), all of which have one assay on their surface. These SMPs are run through a flow cytometer after running an assay protocol. The flow cytometer has a flow cell which differentiates individual SMP events as they go by. Thus, the result is a statistical sampling of the population of the SMPCS made up of individual readings. These individual event readings are not identical, but are distributed in an approximate normal curve. Conventionally, most of these SMP-based assays use fluorescent reporter molecules to provide a signal, but there are other methods. If multiple SMPCSs are present in a well, then more than one analyte can be assayed simultaneously in the same assay plate well. This is termed multiplexing of assays, and it is a primary selling point for current suspended microarray systems.

A multiplexed assay comprises different suspended SMPCSs—where each SMPCS has an assay for a different analyte, and the SMPCSs are mixed together in one test tube or assay plate well. Conventional assay plates currently contain up to 96 wells in one plate, wherein each well contains fluid to be assayed, as shown in prior art FIG. 5. In use, each of the 96 wells in the plate is loaded with some analyte in a fluid medium. Into each well are injected suspended microarray particles with assays on them, and then an assay protocol is performed. Finally, the 96 well plate is inserted into a robotic sampler that feeds a reading instrument. Typically, the reader is a flow cytometer. The robotic sampler inserts a hollow probe, column by row, one well at a time, sucking up a sample of fluid mixed with SMP's, moving the sample acquisition probe from one well to the next.

Another assay method is an environmental assay method sometimes known as "smart dust" which consists of a tiny electronic chip, (that can be microscopic) that has an assay built into it, generally on its surface. This assay device usually receives energy from the environment in the form of sunlight, or from a reader device in the form of microwaves. The device acts as a transponder, sending the result of the assay to the reader device. Some of these devices work in fluid, while others broadcast the particles ("smart dust") over a region which may be outdoors. These broadcast assays indicate to the reader what is present in the environment. There are many identical copies of each assay particle in a broadcast system, and the signals returned can be analogous to signals returned by microspheres in a flow cytometry system, having many separate readings for the analyte that are combined to produce one value. In an environmentally broadcast assay system of this kind the equivalent of the test tube or well in a plate is the responding region containing particles that fall within an area the reader can detect. As the reader is moved, this area changes as particles are added on the leading edge of movement, and lost on the trailing edge. Totalizing of readings for a region can occur by making arbitrary distinctions between one such region and the next. In this type of system, as with fluid suspensions, a set of SMPCS assays could be created where each assay reacted to the same analyte. The results could be collated and processed in an analogous manner to that of intraplex assays taking place within a fluid medium.

One typical flow cytometry system for reading assays is the Luminex® system. To compensate for highly fluctuating readings, it is necessary that multiple wells be replicated for identical samples so that any variation may be seen. Typically this is done with two wells containing identical analyte samples, but this is of little statistical significance, because the "student t test" (hereinafter either "t test" or "t values")

value for a sample of just 2 has a multiplier of more than 60 on the standard deviation (at 99% confidence level) to get margin of error as shown in FIG. 4B. A t value is the statistical multiplier used on standard deviation to decide how wide the margin of error should be for sample sizes of 30 or less. (Use of t test rather than statistics appropriate for samples of more than 30 is not a limitation of this application, rather, for practical reasons, most of the time numbers will be in the t test range.) In part because statistically the accuracy does not improve much when two wells are used, and three wells costs as much as ELISA, most usually, for efficiency and simplicity, only one well samples are performed. One method routinely used for improving the precision and statistical significance employs a number of replicated sample wells coupled with 3 or more pairs of wells as standards, the standards having an increasing level of dilution so as to define a ratio that will correspond to analyte concentration. See FIG. 5. However, using replicates cuts into the cost effectiveness of suspended microarray assays, and can even make them more expensive than ELISA assays. Based on recent findings regarding the above-indicated lack of precision, using even more SMPs has been proposed by Luminex® to further increase precision. See Jacobson J W, Oliver K G, Weiss C, Kettman J. Analysis of Individual Data from Bead-Based Assays ("Bead Arrays"). *Cytometry Part A* 2006;69A:384-390. However, as described below, experiments have shown this method to have significant problems.

In multiplexing, the primary problem with using radically more SMPs for each SMPCS is that when assays are multiplexed there will be a statistical distribution of SMP counts obtained for each SMPCS in the multiplex. Theory predicts this effect, and experiment confirmed it. Thus it was found that to get a fairly reliable number of SMPs for each SMPCS when they are multiplexed an increasing number of SMPs for each SMPCS needs to be put into each sample well. This number of SMPs per SMPCS rises nonlinearly with the number of SMPs one attempts to collect for each SMPCS. In order to explain the problem better, an illustrative metaphor will be used of a swimming pool filled with M&Ms of different colors. In this example, the swimming pool is analogous to a single-sample well, and one M&M is analogous to an SMP. The populations of M&Ms that are of the same color are analogous to an SMPCS.

For this thought experiment, a swimming pool filled with M&Ms of 100 different colors is considered. An equal number of M&Ms of each of 100 colors is present and it is assumed the M&Ms are randomly mixed having no artifacts such as differential density of one color M&M leading to concentration at the bottom or top. A barrel of M&Ms is randomly scooped from the random assortment in the pool, and from the barrel, a large coffee can full of randomly scooped M&Ms is taken. Finally, all M&Ms in the coffee can are thrown high into the air, and those that land within an arbitrary 6-foot diameter circle are categorized. This 6 foot diameter circle corresponds to what is read by a flow cytometer that is able to categorize by color.

What will be seen from the above thought experiment is that there will not be an equal number of each color of M&Ms in the 6-foot circle. If one collects the counts of each color, and then categorizes them into a histogram with 5 to 20 different bins, plotting number of M&Ms in the histogram bin on the X axis against number of M&Ms per color for each bin, what would be seen is an approximation of a multinomial distribution of counts. Assuming the coffee can holds approximately 50,000 M&MS, FIG. 4A depicts a graph of the expected multinomial distribution. It is assumed in this example that 500 M&Ms of each color are desired.

What this multinomial distribution graph shows is that for about 30% of the colors, the number of M&Ms for each color will be near 500. But for some the counts will be much higher, and for some much lower. See FIG. 4A. In order to make reasonably sure that for 95% of the colors, 500 M&Ms are obtained, it is necessary to use a much larger coffee can. This graph also shows that the coffee can holding 50,000 M&Ms will be correct for a large-scale multiplex that has a minimum of 100 M&Ms of each color. What is not shown in this graph is that if the trials are repeated many times, once in a while outliers on both ends may appear, with even lower counts, or else very high counts.

In the case of the Luminex® flow cytometer, we know that the above "trial" will be repeated many thousands of times in the lifetime of an instrument. Understanding the statistical problem encountered in the swimming pool thought experiment makes the problem of SMPCSs in a multiplex assay easier to understand.

One Luminex® instrument, the new FlexMAP 3D™ can differentiate up to 500 different microsphere classifiers. If one were to create a multinomial simulation graph for that many microsphere classifiers, the outliers would be farther to the low and high regions of the graph. The intent of Luminex® in raising the number of classifiers is to allow the development of very highly multiplexed assays. However, if this capability is used, then it will show this distribution of counts problem even more than the current system that relies on 30 to 100 SMP reading events per SMPCS. It will require huge numbers of SMP's per SMPCS to work reliably.

There is thus a need to improve the precision of such assays without replicating samples, and to compensate for the multiple stochastic and non-stochastic sources of errors.

It is therefore a primary object of the invention to improve the precision with which each analyte can be read in any type of suspended array assay system by using a plurality of SMPCS readings for each assay.

It is a further object of the invention to provide a method to compensate for the multiple stochastic and non-stochastic sources of errors that can occur in this type of assay system.

It is a still further object of the invention to make possible statistically significant results from assays applied to single well samples. Since there is no statistical significance to a single result, (see FIG. 4B) and this method has more than one result, it represents an improvement over all assays in which a single result is used.

It is a still further object of the invention to make possible processed readings that have high correlation between instruments, even if the instruments have significantly varying responses to identical stimulus. Experiments have shown that instruments can vary significantly when reading exactly the same SMPCSs.

Other objects and advantages of the present invention will become obvious to the reader and it is intended that these objects and advantages are within the scope of the present invention.

SUMMARY OF THE INVENTION

This present invention provides a method for making readings from a single sample statistically significant in a reliable manner. The method can be applied to any type of suspended array assay systems that use a plurality of individual readings from small (generally microscopic) particles coupled to an assay. This invention combines multiple separately identified assays of one sample, wherein the multiple assays are for a single analyte. By elimination of outliers, averaging, taking secondary averages of averages, taking ratios of averages and ratios of secondary averages, this method makes highly reliable diagnostics possible. This method compensates for the multiple stochastic and non-stochastic sources of errors that can occur in this type of assay system.

The Applicant's method provides more precise readings and diagnoses various errors in these types of assays. Potential sources of variance that can be compensated for include: variation in size of SMPs affecting strength of signal, carry-over of SMPs between wells, and inter-instrument calibration differences (including response curve for varying concentrations of analyte by the complete opto-electronic system.) Another problem that can be addressed by this method is the distribution of varying counts per SMPCS that occurs due to stochastic variance in multiplexed assays.

The advantages of the Applicant's system are that the system (1) increases the statistical significance of results from assays applied to single well samples, (2) makes possible compensation for multiple sources of error, (3) makes possible increased precision for each analyte, and (4) makes possible processed readings that have high correlation between instruments, even if the instruments have significantly varying responses to an identical stimulus.

A first form of the Applicant's method is what is known as a first-order intraplex assay, in which there is a set of m SMPCSs assaying for the same analyte where the assays are titrated to give different responses to the same level of analyte. A second-order intraplex is also detailed. This is an m×n matrix in which m different SMPCSs with coatings titrated to give different response levels have n duplicated SMPCSs that should give the same response. Finally, a multiplexed intraplex example is detailed, in which intraplex assays are combined so that multiple different analytes can be assayed following the Applicant's novel method.

BRIEF DESCRIPTION OF THE FIGURES

The foregoing aspects and many of the attendant advantages of the invention will become more readily appreciated as the same becomes better understood by reference to the following detailed description, when taken in conjunction with the accompanying drawings, wherein:

FIG. 3A-3C shows the processing of the intraplex from FIG. 2 using a simulated example.

FIG. 3A (Step 1) shows the m=4×n=5 SMPCS reading dataset graph for all SMPCSs, 001-020. In this diagram, the n axis is labeled S1-S5 to denote the indices of n for all the members of the SMPCS-IDG dataset. The m axis is labeled IDG1-R to IDG4-R to indicate the readings for the SMPCS-IDGs in the dataset. The outlier at IDG1-R, S5 is removed from the set of n of SMPCS-IDG 1. This changes the result when the mean of the set of n SMPCSs is calculated in Step 2 below. Completion of Step 1 is removal of outliers that are identified.

FIG. 3B (Step 2) shows the result of this step is m averages, (means of the sets of n SMPCSs) using as input the n microsphere set fluorescence readings for each SMPCS-IDG. The resulting mean of the set of n SMPCSs data is shown in the table. Each of these 5 means of the sets of n SMPCSs are then averaged together to give a single mean of the set of m SMPCS-IDGs.

FIG. 3C (Step 3) shows the internal self mean ratios calculated using the mean of the set of m SMPCS-IDGs as denominator for each of the means of the sets of n SMPCSs, from the calculations of step 2. This is done in the same way as for the first-order intraplex of FIG. 1.

FIG. 5 is a diagram of a typical 96 well assay plate, having rows A-H and columns 1-12. This is supplied for illustration purposes to help visualize the current art. The section in the upper left with a line drawn around 5 pairs of wells D is an example of an area of a multi-well plate that would be used for inserting standards for generating a standard curve for the plate. While wells D is shown by way of example, the number of standards wells used in practice varies depending on how detailed the standard curve is desired to be.

DETAILED DESCRIPTION OF THE INVENTION

Figure 1A:
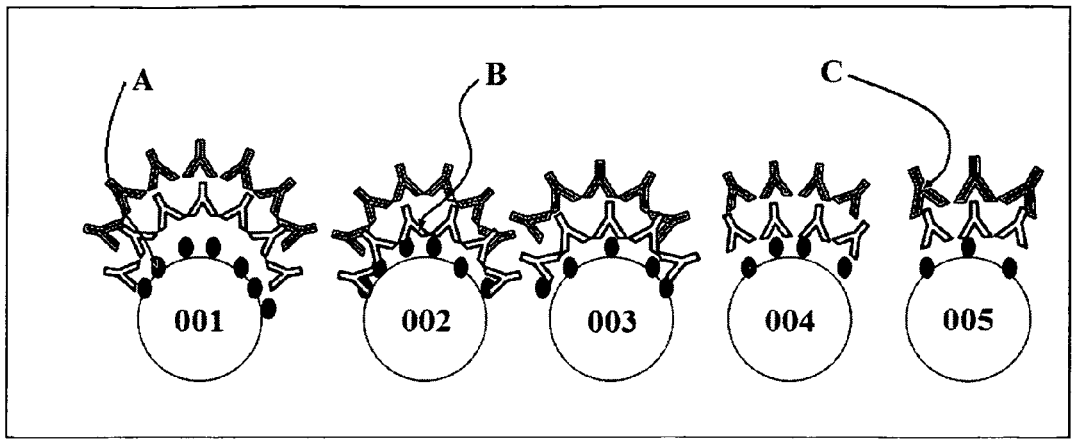
FIG. 1A depicts a first-order intraplex concept diagram showing idealized characteristics where m=5 different microsphere sets (i.e. 5 SMPCSs) labeled 001 to 005. A classic sandwich assay is shown on the surface of microspheres, by way of example, although many different assay methods could be used. Different densities of ligand (in this case antigen, A) to bind analyte (in this case antibody, B) are coated on the microspheres. One way to vary coating density is by consecutive dilutions. So, more binding sites are available for a target antibody analyte on those microspheres incubated with higher concentrations. Secondary antibody with fluorophore, C, binds to analyte, B, to provide a signal to the flow cytometer.

The Applicant discloses several intraplex embodiments and provides guidance for the method to be applied to other situations. Although it will be described in relation to suspended microarray assays using a typical 96 well assay plate which typically suspend particles in fluid before reading the result via flow cytometry, the method may be applied to a variety of different types of particulate based microarray assays using various numbers of samples. In such assays, an assay is bound to the particle surface, and a protocol is run that results in a signaling event such as fluorescence indicating presence of analyte. Such assays include microspheres, microbeads, magnetic microbeads, bar-coded microrods, and microtransponders. ("Smart dust" is the distribution of tiny assay devices coupled with miniature transponders, where the sampling is of the environment, and it can also make use of the intraplexing method.) It is not necessary that the physical or chemical method of assaying for a specific analyte be identical on each of the suspended microarray intraplex assays. It is only necessary that the end result be a predictable difference in response signal level for a given concentration of analyte for each of the m assays.

For purposes of the patent application, the term "intraplexing" and "intraplex" shall refer to the execution of the applicant's method. An "intraplexed assay" is one in which the intraplexing steps as defined have been performed.

An SMP is a suspended microarray particle. This is one particle, such as a microsphere, microbead, a microrod or some other microscopic particle assay device that can be suspended in a liquid medium, or broadcast over some area.

An SMPCS is a suspended microarray particle category set. This is a population of a multiplicity of microscopic particles such as microspheres, microrods or some other microscopic assay device, (see SMP) which has a marker system to allow categorization of a set by a reader instrument. In the Luminex® system, this is done by using two different long wavelength fluorophores that are varied as to proportion so that the set of particles can be categorized. The resulting two-dimensional matrix has regions to which numbers are assigned and can differentiate up to 100 different categories. As stated above, the Applicant's methods apply to a variety of situations, such as that involving a new instrument able to differentiate up to 500 different categories.

Finally, an SMPCS-IDG is a suspended microarray particle category set identical group. This is a multiplicity of SMPCSs (see SMPCS) all of which share an identical signal response level to a single analyte being assayed.

The "mean of the set of n SMPCSs" shall refer to the average of all the SMP category sets (SMPCSs) in an intraplex that comprise an SMPCS-IDG. By extension, "means of the sets of n SMPCSs" shall be the plural form.

The "mean of the set of m SMPCS-IDGs" shall refer to the average of all the SMPCS-IDGs in an intraplex that have different level of response titration. A "mean of the set of m SMPCS-IDGs" may use a set of one or more "mean of the set of n SMPCSs" as its input, where each "mean of the set of n SMPCSs" defines on of the m values used to calculate the mean of the set of m SMPCS-IDGs.

"m ratios" shall refer to the set of ratios of mean of the set of n SMPCSs as numerator, over mean of the set of m SMPCS-IDGs as denominator, which are m in count.

The "range of m ratios" shall be defined as the absolute value of each ratio to each of the other ratios in the set of m ratios.

"SMP event readings" shall refer to the set of individual events detected by an instrument used to detect the signal(s) from a set of microparticles on which an assay has been attached.

"SMPCS readings" shall refer to the processed results presented by an instrument system that is used to evaluate some signal (which could be some radio frequency, fluorescence or some other detectable physics) from a set of SMP events. Typically, this would be presented as an arithmetic mean, a median, a peak (which is analogous to mode) or something similar. A user may have a choice of which of the values presented by the instrument system they will choose to use. When user choice is allowed, all of the choices available are considered "SMPCS readings" if they are used. A user might wish to further process the set of available SMPCS readings into a single numeric value, and if this was done, that value would also be considered an "SMPCS reading".

"SMPCS value" is an alternative way to refer to a number representing the result of an assay for a sample of a population of microparticles, as detected by an instrument system.

The term "classifier" shall refer to the code that is used to identify all of the SMPs within one SMPCS. By extension, the term "classifiers" shall be the plural for a multiplicity of SMPCSs. (I.e. in the Luminex system, these are numeric values from 001 to 100 that are based on the technology of varying intensity of two fluorophores.)

Figure 1B:
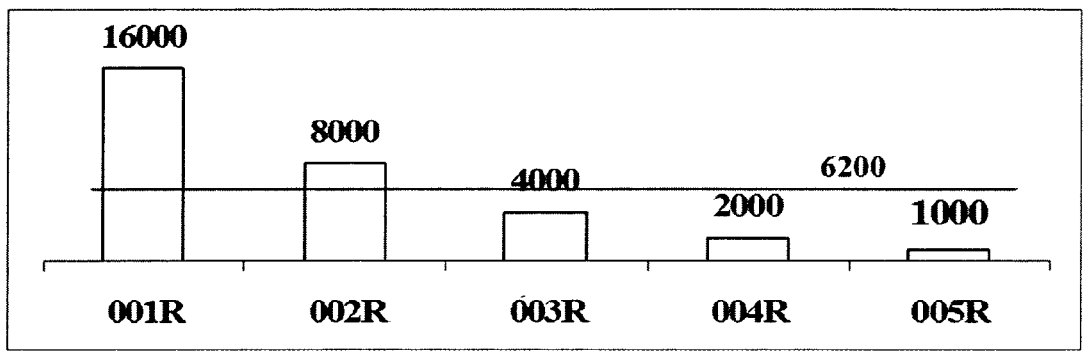
FIG. 1B shows simulated reporter fluorescence readings, as processed by the instrument, for an assay that reflects 2× series dilutions of ligand bound to microspheres showing how each SMPCS responds differently to the same concentration of analyte. In this diagram, 001R corresponds to the instrument reading for SMPCS 001 of FIG. 1A, 002R corresponds to the instrument reading for SMPCS 002, and so on. Mean of the set of m SMPCS-IDGs=6200 is denoted by horizontal line. This mean is the internal self mean of the m fluorescence readings.
Figure 1C:
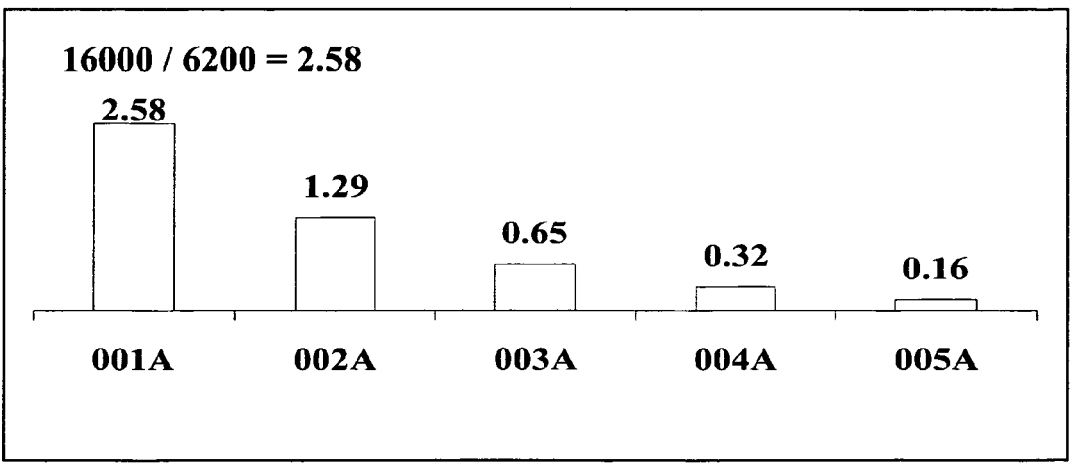
FIG. 1C shows internal self mean ratios for each of the 5 SMPCS instrument readings of FIG. 1B. An example calculation is shown for SMPCS 001. In this diagram, 001A corresponds to the ratio of 001R to the internal self mean of the m instrument readings, 002A corresponds to the ratio of 002R, and so on. The mean of the set of m SMPCS-IDGs is used as the denominator for each of the m fluorescence readings obtained by an instrument.

A first embodiment of the Applicant's system shall be referred to as a first-order intraplex assay, in which there is a set of m assays for the same analyte. In this case a single copy of each assay is used (i.e. n=1). As shown in FIG. 1A-1C, said first-order intraplex is an antigen on microsphere type assay. This is one type of assay used and is presented here as an example only. In this type of assay, a large antigen molecule A is attached to the SMPs. Serum antibodies B, attach to the antigen molecules A. Reporter antibodies C attach to serum antibodies B, and these reporter antibodies have a fluorophore attached. When illuminated with laser of the right frequency, the reporter fluoresces, which the flow cytometer reads as an intensity level. Here, each assay is titrated during the assay manufacturing process to give a different response to the same level of analyte. The readings comprising multiplicities of SMP event fluorescent intensities are shown as a chart in FIG. 1B. This will typically be performed by coating them in differing concentrations of whatever detection chemistry is needed in order to detect an analyte. FIG. 1C diagrams the concept of one type of ratio, the internal self-mean, which was determined by experimentation to be stable for generating replicated single tube assay readings. This ratio is stable between instruments and between wells, even when absolute readings vary dramatically from each other due to a wide variety of calibration problems. For purposes of claim construction, this internal self-mean will be referred to as the "mean of the set of m SMPCS-IDGs."

Figure 2:
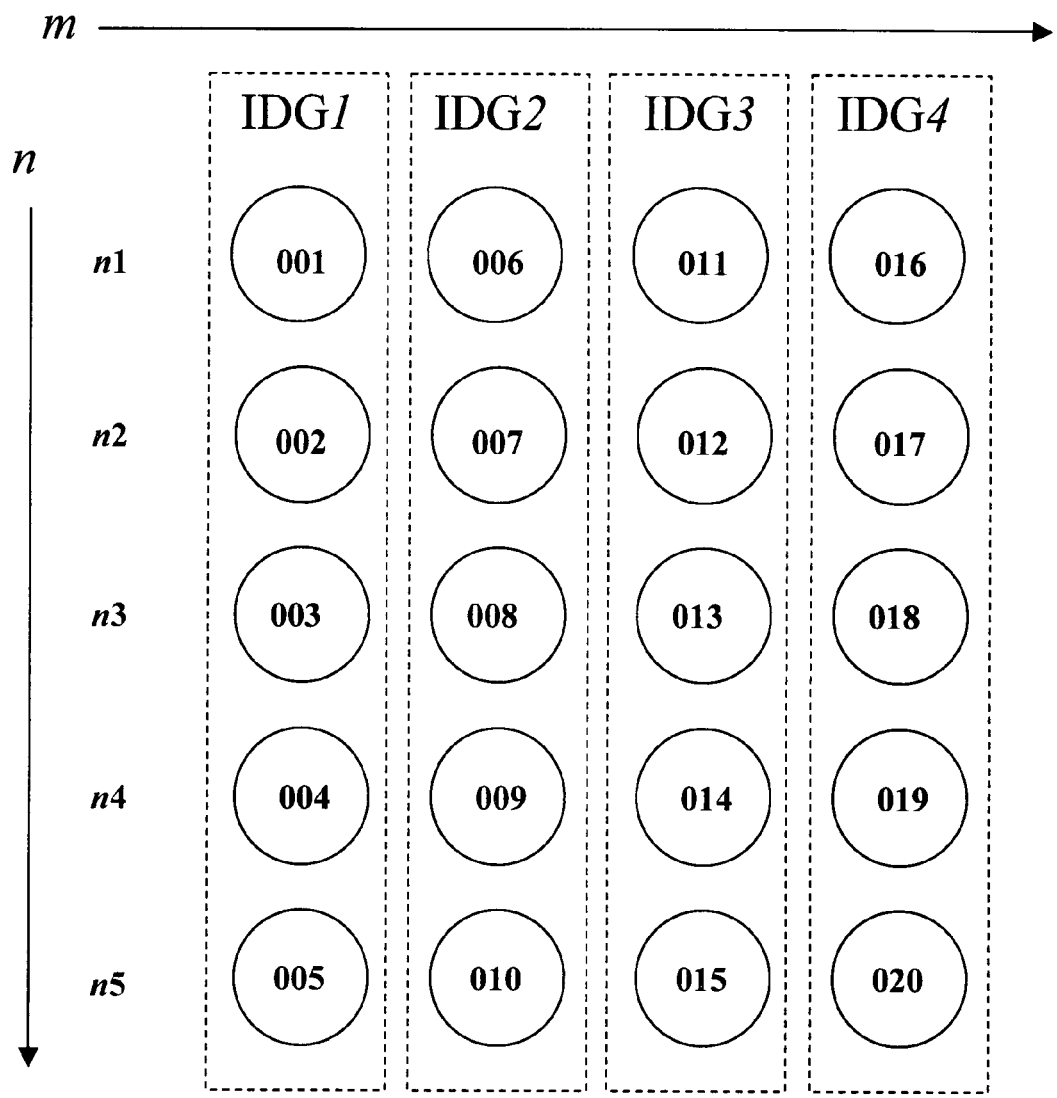
FIG. 2 is a diagram conceptualizing a second-order intraplex, an m×n SMPCS based assay, where the SMPCSs are microspheres. Each circle in this diagram represents an SMPCS. The set of m is a composed of 4 SMPCS-IDGs labeled across the top, IDG1-IDG5 with each member of the set outlined with dotted lines. Each SMPCS classifier's label is within each circle. Each of n (001 to 005 for SMPCS-IDG 1, 006 to 010 for SMPCS-IDG 2, etcetera.) SMPCSs that make up the SMPCS-IDG for each of m sets is designed to show identical sensitivity. (However, in practice, there is always variation.) Down the left side of the diagram are shown the indices of n, as n1-n5 for reference. Like FIG. 1A, the m SMPCS-IDGs would be manufactured using serial dilutions (or some other useful difference in sensitivity method).

The preferred embodiment, a second-order intraplex is an m×n matrix in which m different SMPCS response titrations have n identical SMPCS assays, as shown in FIG. 2. In FIG. 2, each circle in the diagram represents a set of microspheres (i.e. an SMPCS). Each of the superset identical groups (i.e. SMPCS-IDGs) (m=4) is coated at different sensitivities. The SMPCS-IDGs of m are across the top, labeled IDG1, IDG2, IDG3, and IDG4. Note that now each m is a superset comprising 5 microsphere set classifiers (i.e. an SMPCS-IDG). Each of n (01 to 05 for SMPCS-IDG 01, 06 to 10 for SMPCS-IDG 02, and so on) microspheres that make up the superset SMPCS-IDG for m is coated in the same batch for identical sensitivity. Like FIG. 1A, the m SMPCS-IDGs have serial dilutions (or some other useful difference in sensitivity method) in their manufacture. FIG. 3A-3C shows processing of the intraplex using a simulated example. 3A-Step 1: An m=4×n=5 fluorescent reporter reading dataset graph for all SMPCSs, 01-20. The readings for the set of m are denoted by IDG1-R, IDG2-R, IDG3-R, IDG4-R. (Note the outlier at {IDG1-R, S5} that was removed for the set of n for the m IDG1-R for the next calculation step.) Completion of step 1 is removal of outliers should they be present. 3B-Step 2: The result of step 2 is m averages, (means of the sets of n SMPCSs) using as input the n microsphere set readings for each SMPCS-IDG. This is shown in the table. Each of these 4 means of the sets of n SMPCSs is averaged together to give a single mean of the set of m SMPCS-IDGs. In this table, m01 corresponds to mean of IDG1-R, m02 corresponds to mean of IDG2-R and so on. 3C-Step 3: Internal self mean ratios are taken using the mean of the set of m SMPCS-IDGs as denominator for each of the means of the sets of n SMPCSs from step 2. In this diagram, 01 corresponds to a ratio made with m01 as numerator, 02 corresponds to a ratio with m02 as numerator, and so on. This is done in a similar way as for the first-order intraplex of FIG. 1.

Note that it is not required that the number, n, of identical assays be the same for each of the m different response titrations.

In summary, the intraplex method diagrammed in FIG. 3A-3C includes mathematical and statistical processing steps including (3B) to remove outliers from n values if they are present. (3C) averaging of remaining values from the n set to produce m means of the sets of n SMPCSs and further averaging the m means of the sets of n SMPCSs to produce a mean of the set of m SMPCS-IDGs. (3D) taking of ratios between the each of the m means of the sets of n SMPCSs, and the mean of the set of m SMPCS-IDGs.

Figure 4A:
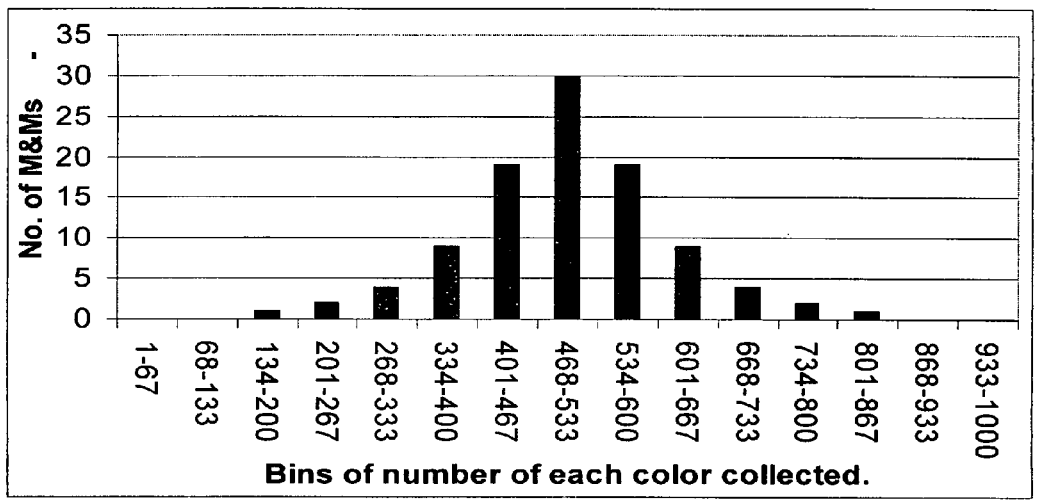
FIG. 4A is a multinomial distribution graph providing clarification for a problem inherent in the prior art.
Figure 4B:
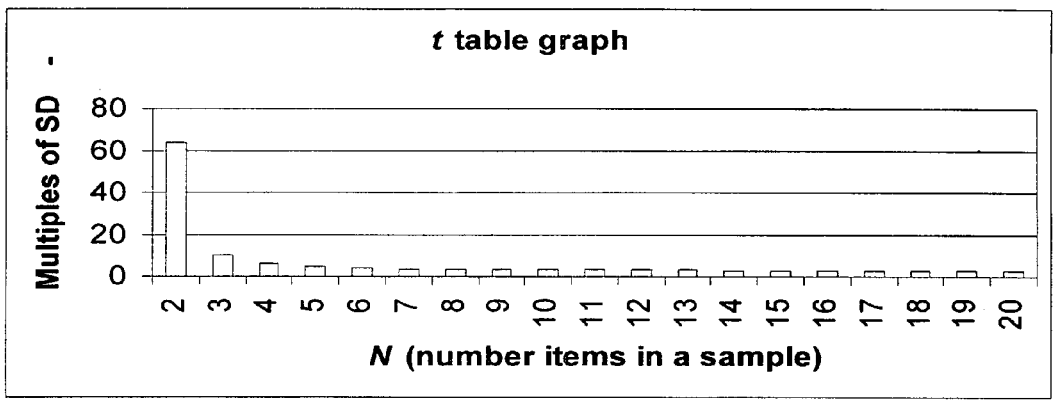
FIG. 4B is graph providing clarification for a problem inherent in the prior art. This graph shows t values for an α=0.01 (99% confidence)

Additionally, a third embodiment, a degenerate second-order intraplex where m=1 containing only one set of n>1 (usually n will be >2, see FIG. 4B) identical assays, will still be more reliable when the average for the n readings is used in place of the single reading used currently. In this case, a simple two-step process will be used including (1) removing of outliers from the n values, (2) averaging of the remaining values from the n set to produce a useful reading.

Intraplex assays can be combined so that multiple different analytes can be assayed in this manner and is referred to as a multiplexed intraplex. For example, five different analyte assays, with each assay consisting of a 4 by 4 intraplex for each analyte could be combined. This combination would require a total of 64 SMPCSs, 16 SMPCSs for each intraplex assay. Intraplex assays can also be combined in a multiplex manner with single SMPCS assays according to current convention. The following relates to a preferred embodiment of the invention as shown in FIGS. 1 and 2.

The physical embodiment of an intraplex assay system for placement of an assay on microparticle media for reading by an instrument comprises a plurality of SMPCS assays, each providing a separate reading and wherein each reading is obtained in a manner standard for the instrument normally used to read it. This plurality of assays comprises a number (m) of SMPCS assays targeted at a common analyte wherein each SMPCS assay has a different response level to said analyte when said SMPCS assay is conducted. There are also n SMPCS assays that are copies of each of the m SMPCS assays, where each of the n copies is designed to show identical signal level for a given level of analyte. Finally, both m and n may be an integer of at least 1, m and n are not required to be the same, and the n for $m_p$ is not required to be the same as the n for $m_q$ where q and p are subscripts, each identifying an $m_i$ group of SMPCSs. (I.e. an intraplex may have 5 identical copies of one response level and 4 identical copies of another.)

In typical operation, any SMPCS assays are added into a standard well in an assay plate, or to another test-tube analogue. The assays are read by an appropriate instrument for the microparticle system this assay method is applied to. For some SMPCS assays this could be any flow cytometer, for others it may be best achieved by using a specialized flow cytometer optimized for a particular set of identification markers. These readings are interpreted by software that is informed of how reading sets should be grouped for each intraplex assay. The software may have pre-set calibration response curves and margins of error for each intraplex assay as defined by the manufacturer. The software performs appropriate statistical processing on the set of intraplex readings, and returns a set of values to the user of the software, which represents the intraplex assay results. These results may be correlated by the software with a range of concentrations for the analyte in question. Software is not strictly necessary, it is a convenience. Analysis may be done by hand, by spreadsheet, statistics software or some special-purpose software. The analysis results in either a reading showing a signal level, which is compared to some standard value range, or a concentration, such as picograms per milliliter interpolated from a standard curve.

In an alternative embodiment of the invention, there is some flexibility in the three algorithmic processing steps. In step one, the algorithm for determining whether an individual reading of a set is an outlier can vary. In step two, the averaging method used may not be a simple arithmetic mean, but instead one of a variety of other methods for determining an average, such as arithmetic mean, geometric mean, harmonic mean, or quadratic mean. All of them can be used to produce different numerical results that can then be used, as long as they are used with appropriate consistency. In step three, ratios may be taken between the available averages. What is important is that the basic concepts are applied. A software developer may choose any variants they find useful, including elimination of a step.

Figure 5:
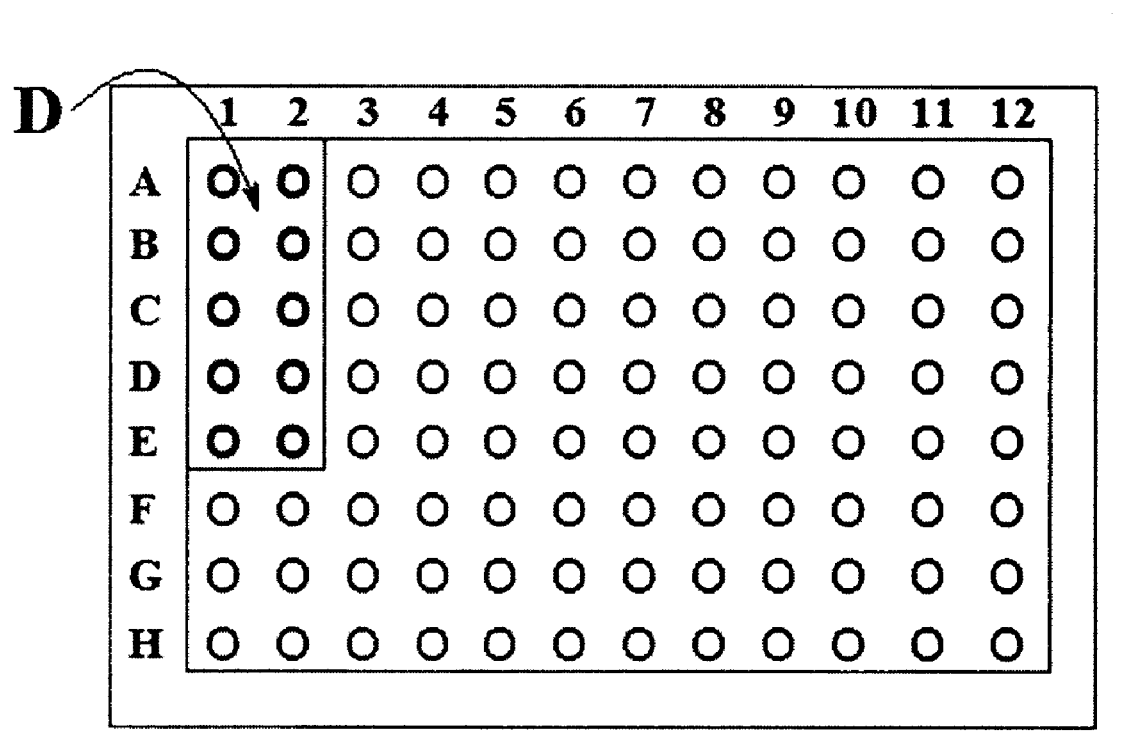

A fourth step may be performed that provides a concentration estimate for intraplex assays. Typically, a standard curve is made for each assay plate. As shown in FIG. 5, a typical 96 well assay plate having rows A-H and columns 1-12 may be used. Fluid samples are placed in each of the 96 wells. Col. 1-2 Rows A-E, highlighted in bold in FIG. 5, are standards wells. A typical set of standards for a plate such as that shown in FIG. 5 would be 6 pairs of wells, where each pair of wells contain identical concentrations of the calibration standard fluid, and successive pairs are sequential dilutions. The standard fluid contains known quantities of analytes. Typically, the first pair of wells contains a full strength standard fluid, the second pair is diluted 1:2, the third pair is diluted 1:4, fourth pair is diluted 1:8, and fifth pair 1:16. SMPCSs for the desired analytes are injected into all wells, both standard containing wells and sample containing wells. The pair of readings for each titration of the standard wells is averaged and the 6 averages used to generate a "standard curve." Using the standard curve, readings from other wells in the plate can be interpolated as to their concentration.

For an intraplex concentration estimate, an assay developer can create a standard curve for the assay using several plates, each of which contains as many wells as possible for the standard curve. Instead of 5 or so titrations for which interpolation is done, a large number of titrations, perhaps as many as 90 or more could be made. These standard curve plates can be repeated as many times as the assay manufacturer deems useful to ensure reliable results. Such a standard curve plate or plates can be run for each batch lot of intraplexed assays, and generally would be as a quality control method. Note that in this way it is not strictly necessary that a manufacturer replicate each of m response levels precisely, since they would recalibrate their assays for each batch lot. The developer can then define estimated concentration of analyte and margin of error by correlating known concentration with such features as the range of m ratios, fitting curves to the ratios by numerical methods or derivatives of the curves fitted, when ratios are graphed as points where the y coordinate is the ratio and the x coordinate is a useful value selected by the developer for each of the m ratios. For instance, given a set of m ratios as shown in FIG. 3C, of {2.19, 1.09, 0.55, 0.27} as y coordinates, a developer might choose {1, 2, 3, 4} as the respective x coordinates. In such ways, a developer would produce a "predetermined calibration dataset". Within this dataset could be ratio ranges, fitted curves, derivatives of fitted curves for use in evaluating estimates of concentration of analyte for intraplex assays.

An additional method that could be used for estimation of concentration of analyte is clustering of ratios using a K nearest neighbor algorithm or a neural net system. In K nearest neighbor, the ratios are used as N dimensional vector sets. This transformation into an N dimensional vector set can be done in a variety of ways which would be up to the software developer. Each vector set defines a point in N dimensions, and is then assigned a meaning value. The meaning response value would be a concentration. When a new vector set is supplied to the system, it also defines a point in the N dimensional space. The algorithm then returns the nearest neighbors as limited by a value, d, which is a maximum distance in the N dimensional space for any responders. The response is composed of a set of meaning values, each paired with vector distance from the new value. This allows an interpolation to be performed using the meaning values.

Example of a K nearest neighbor system (Knns) in use. For this example we will use a simple 2 dimensional plane with x and y coordinate axes. The Knns is "trained" by supplying it a series of 4 vector pairs. These are: |{1,0}, {2,1}, {3,1}, {4,2}|. These four pairs are assigned meaning values of: {0, 5, 7, 10} respectively. To use the Knns a pair of numbers is supplied, {3,2} using a distance, d, of 2. The system would then find the points within a circle of radius 2 from {3,2} and return three value pairs consisting of: {meaning value, distance}|{5, 1.4} {7,1} {10,1}|. This is because the point {3,2} is a distance of 1.4 from {2,1}, and a distance of 1 from both {3,1} and {4,2}.

This calibration dataset from the developer can be supplied with an assay kit so that estimation of concentration from intraplex results can be performed either manually by the user, or by software. It might be desirable for an assay manufacturer to automatically download calibration datasets into intraplex interpretation software based retrievable by assay lot identifier.

It has been determined that intraplex assay results are highly stable from instrument to instrument, and can even compensate for variability in sensitivity of a single instrument over one assay plate. Consequently, intraplex assays do not necessarily require the use of standard fluids and standard curves on every plate to determine concentration of analytes. This provides opportunities for logistical improvement in certain diagnostic tests. Where standard curve methods are used for every plate of samples, intraplex derived concentration estimates can provide a crosscheck on the usual standard curve system.

The intraplex invention has wide application for providing high precision assays that are typically read by flow cytometry. This type of assay is applicable also to assays such as "smart dust" and others that may not be suspended, but are instead distributed over some region to assay for analytes. The limit of the type of assay that this is applicable to is assays wherein the reading is made up of a collated set of readings from small particles. Those small particles may be of variable shape, and the particles have a means for providing a signal indicating the level of analyte detected.

Now that the steps involved in the applicant's method have been adequately detailed, several example implementations of the steps will be described. For each of these examples, it is assumed that (1) there is no significance to the SMPCS classifiers selected being consecutive, only that they are different from each other, and (2) there is no theoretical reason why numbers of SMPCS classifiers would not be as many as 300 or more for a single intraplex assay in its entirety. To further explain point two, statistics indicates rapidly diminishing returns for larger numbers, but in physical terms limits are practical. The choices below are guided by what would be the low end numbers that statistically would show significant improvement in precision and reliability of suspended microarray assay systems.

EXAMPLE 1

A simple first-order intraplex. Although this is not the preferred embodiment of the applicant's system, this example implementation is described first for purposes of simplicity. In this example, m=6, meaning 6 different SMPCSs are used. In the Luminex® system, microspheres are used for the SMPs, and one could select SMPCS 001, 002, 003, 004, 005 and 006. Using standard methods as described by Luminex®, some chemical, antigen, hapten, antibodies, or oligonucleotides are attached to the surface of the SMPCSs. For SMPCS 001, a chemical coating concentration is applied in the reaction vessel that will occupy the maximum available binding sites on the SMPCS. For the second SMPCS, the concentration of the coating chemical is diluted so as to provide less than complete occupation of available binding sites. A typical dilution factor might be 2, 3, 10 or whatever is determined to work appropriately. Each SMPCS in turn is coated with a serial dilution such that the end result will be 6 SMPCSs, wherein each of the 6 SMPCSs is coated so that they should give different signal level response to the same analyte. After the coating steps are complete, the SMPCSs are combined together and injected into the assay plate well so as to provide the same number of SMP's for each SMPCS (for instance, if there are 2000 of SMPCS identifier 001, then there are 2000 of SMPCS identifier 002, etc.)

Each SMPCS will present a distribution of readings. In the Luminex® system, a variety of information is presented to the user, including mean and trimmed mean, peak and trimmed peak, (which are similar to mode) and median and trimmed median. It is often recommended to use median. In practice, it makes little difference which is used as long as the choice is consistent. Whichever value is chosen for use, that value becomes the reading from the instrument for the SMPCSs. A first order intraplex-average (mean of the set of m SMPCS-IDGs, where in this case n=1 for each m SMPCS-IDGs is then calculated from the 6 SMPCS values. After this, 6 ratios are then taken with the SMPCS reading as the numerator and the master average (mean of the set of m SMPCS-IDGs) as the denominator.

EXAMPLE 2

A second order intraplex. In this preferred embodiment and example, m=4 and n=5, meaning 20 SMPCSs are selected. In the Luminex® system, microspheres are used for the SMPs, and for purposes of this example one could select SMPCS 001 to 020. The SMPCSs are then divided into 4 subsets of 5 SMPCSs each. (Each set of 5 will be an SMPCS-IDG.) For each of the 4 subsets of 5 microspheres, all 5 microsphere sets are combined in a reaction vessel. Using standard methods as described by Luminex®, some chemical, antigen, hapten, antibodies, or oligonucleotides are attached to the surface of the microsphere sets. For the first identical group subset of 5

SMPCSs, (first SMPCS-IDG) a chemical coating concentration is provided in the reaction vessel that will occupy the maximum available binding sites on the SMPCSs. For the second subset of 5 SMPCSs, the concentration of the coating chemical is diluted so as to provide less than complete occupation of available binding sites. A typical dilution factor might be 2, 3, 10 or whatever is determined to work appropriately. The end result of this will be 4 subsets of 5 SMPCSs, (or 4 SMPCS-IDGs) wherein each of the 5 SMPCSs in a subset are coated the same, but there are 4 different subsets that should give different signal level response to the same analyte. After the coating steps are complete, the 4 subsets of SMPCSs (or 4 SMPCS-IDGs) are combined together and injected into the assay plate well so as to provide the same number of SMPs for each SMPCS.

Each SMPCS will present a distribution of readings. In the Luminex® system, a variety of information is presented to the user, including mean and trimmed mean, peak and trimmed peak, (which peak values are similar to mode) and median and trimmed median. It is often recommended to use median. In practice, it makes little difference which is used as long as the choice is consistent. Whichever value is chosen for use, that value becomes the reading from the instrument for the SMPCSs. For each of the 4 identical group subsets of 5 SMPCSs in turn, (for each SMPCS-IDG) any outlier readings in the subset of 5 SMPCSs may be removed if desired. Then the remaining readings of the subset are used to generate a mean average. This will result in 4 identical group subset averages (4 "means of the sets of n SMPCSs", one for each SMPCS-IDG). Since the assay subsets have varying signal strengths the subset averages will differ.

An intraplex-average (mean of the set of m SMPCS-IDGs) is then calculated by taking the mean of the 4 subset averages. 4 ratios may then be calculated using the subset averages (means of the sets of n SMPCSs) as numerators and the intraplex-average (mean of the set of m SMPCS-IDGs) as denominator.

EXAMPLE 3

A second order intraplex where n is not identical. In this alternative embodiment and example, the intraplex is determined similarly to that in example two above, with the exception that instead of all four subsets having 5 SMPCSs, each subset could have a different number of SMPCSs. For instance, subset A could have SMPCS classifiers 001, 002, 003, or 00. Subset B could have SMPCS classifiers 005, 006, 007, 008, 009, or 010. Subset C could have 011, 012, 013, 014, or 015. Subset D could have classifier numbers 016, 017, 018, 019. (For this alternative embodiment, it is not necessary that all of the subsets have a different number of SMPCSs, only that they are not all required to have the same number.) There are various reasons why an assay developer might want to make use of different numbers of beads. One reason might be that a higher degree of precision might be desirable for lower sensitivity SMPCSs compared to higher sensitivity SMPCSs since for a lower level of reporter signal the signal to noise ratio is lower, and hence a larger number of SMPCSs for that SMPCS-IDG makes sense. Additionally, there might be considerations of simple pragmatism, trying to use fewer SMPCSs, so that a multiplex of intraplexes will fit into the available SMPCSs for the instrument. Or there might be other practical reasons why using an optimum number of SMPCSs might not be reasonable. However, in every other way, the data is processed as in Example 3.

EXAMPLE 4

A degenerate second-order intraplex. In this alternative embodiment and example, m=1 and n=5, meaning 5 SMPCSs are used. In the Luminex® system, one might select SMPCS 006, 007, 008, 009 and 010. The 5 SMPCSs are then combined in a reaction vessel. Using standard methods as described by Luminex®, some chemical, antigen, hapten, antibodies, or oligonucleotides are attached to the surface of the SMPCSs. This will ensure that all five SMPCSs are coated the same. After the coating steps are complete, the SMPCSs are injected into the assay plate well so as to provide the same number of SMPs for each SMPCS. Readings for each SMPCS are then collected as in previous examples. Following collection of readings, a decision is made as to whether to eliminate any outlier SMPCS readings in the set of 5. Then, the average of the remaining readings is taken. The average is the reading that would be used instead of the current single SMPCS value of the instrument.

While the invention has been described in connection with specific embodiments thereof, it will be understood that it is capable of further modifications and this application is intended to cover any variations, uses, or alterations of the invention following. In general, the principles of the invention and including such departures from the present disclosure as come within known or customary practice within the art to which the invention pertains and as may be applied to the essential features hereinbefore set forth and as follows in the scope of the appended claims.

I claim:

1. A method for improving the statistical significance of readings from a single sample, the method comprising:
    a. performing a first assay on a microparticle media for reading by an instrument, the first assay comprising;
        i. m number of SMPCS-IDG assays targeted at a common analyte;
        ii. wherein each said SMPCS-IDG assay is designed to exhibit a different response level to said common analyte;
        iii. wherein each said SMPCS-IDG assay comprises n number of SMPCS assays;
        iv. wherein each said SMPCS assay is designed to exhibit a substantially identical response level to said common analyte;
        v. wherein m is an integer of at least 1 and n is an integer of at least 1;
        vi. wherein if m equals 1 then n is greater than 1 and if n equals 1 then m is greater than 1; and
        vii. wherein m and n are not required to be the same value and n is not necessarily the same value for each m; and
    b. obtaining an SMPCS reading from each said SMPCS assay in each said SMPCS-IDG;
        i. wherein there are n number of SMPCS readings for each of said m number of SMPCS-IDG assays.

2. The method according to claim 1 further comprising the step of removing outlier values from said n number of SMPCS readings if the outlier values are present.

3. The method according to claim 2 further comprising the step of taking one of either an arithmetic mean average, geometric mean average, harmonic mean average, or quadratic mean average of said n number of SMPCS readings to generate m means of the sets of n SMPCSs, one mean of the set of n SMPCSs for each SMPCS-IDG assay.

4. The method according to claim 3 further comprising the step of taking one of either an arithmetic mean average, geometric mean average, harmonic mean average, or quadratic mean average of said m means of the sets of n SMPCSs to calculate a mean of the set of m SMPCS-IDGs.

5. The method according to claim 4 further comprising the step of determining a second m ratio set, comprising m ratios of each of said m means of the sets of n SMPCSs to said mean of the set of m SMPCS-IDGs.

6. The method according to claim 4 further comprising the step of determining a third m ratio set, comprising m ratios of said mean of the set of m SMPCS-IDGs to each of said m means of the sets of n SMPCSs.

7. The method according to claim 3 further comprising the step of determining a fourth m ratio set of any of said m means of the sets of n SMPCSs to any of m averaged readings taken from an assay of a different analyte.

8. The method of claim 5, 6 or 7, further comprising the steps of:
   a. creating a calibration dataset by running multiple samples of known concentrations of said common analyte at different concentrations and
   b. recording for each of said multiple samples of known concentrations of said common analyte:
      i. said known concentration of said common analyte;
      ii. said SMPCS readings from each SMPCS assay;
      iii. said m number for said SMPCS-IDGs in the first assay;
      iv. said n number for the SMPCSs in each SMPCS-IDG in the first assay; and
      v. a list of classifiers for each SMPCS-IDG assay.

9. The method of claim 8, further comprising an additional calibration dataset created by recording summary data: for each said known concentration of said common analyte, for each SMPCS-IDG in said first assay, record one or more of said first m ratio set, said second m ratio set, said third m ratio set, or said fourth m ratio set.

10. The method according to claim 8, wherein range for one or more of said first m ratio set, said second m ratio set, said third m ratio set or said fourth m ratio set calculated from said first assay conducted on a sample are compared to the range of one or more of first m ratio set, second m ratio set, third m ratio set or fourth m ratio set calculated from said calibration dataset to estimate a probable range of concentration of said common analyte.

11. The method according to claim 9, wherein range for one or more of said first m ratio set, said second m ratio set, said third m ratio set, or said fourth m ratio set calculated from said first assay conducted on a sample are compared to the range of one or more of said first m ratio set, second m ratio set, third m ratio set, or fourth m ratio set from said additional calibration dataset to estimate a probable range of concentration of said common analyte.

12. The method according to claim 8, wherein range for one or more of said first m ratio set, said second m ratio set, said third m ratio set, or said fourth m ratio set calculated from said first assay conducted on a sample are compared to the range of one or more of first m ratio set, second m ratio set, third m ratio set, or fourth m ratio set calculated from said calibration dataset to estimate a probable range of concentration of said common analyte using a k nearest neighbor algorithm.

13. The method according to claim 9 wherein range for one or more of said first m ratio set, said second m ratio set, said third m ratio set or said fourth m ratio set calculated from said first assay conducted on a sample are compared to the range of one or more of first m ratio set, second m ratio set, third m ratio set or fourth m ratio set from said additional calibration dataset to estimate a probable range of concentration of said common analyte using a k nearest neighbor algorithm.

14. The method according to claim 8 wherein one or more of said first m ratio set, said second m ratio set, said third m ratio set or said fourth m ratio set calculated from said first assay conducted on a sample are compared to one or more of first m ratio set, second m ratio set, third m ratio set or fourth m ratio set calculated from said calibration dataset to estimate a probable range of concentration of said common analyte by comparing fitted curves based on the m ratio sets mentioned in this claim.

15. The method according to claim 9 wherein one or more of said first m ratio set, said second m ratio set, said third m ratio set or said fourth m ratio set calculated from said first assay conducted on a sample are compared to one or more of first m ratio set, second m ratio set, third m ratio set or fourth m ratio set from said additional calibration dataset to estimate a probable range of concentration of said common analyte by comparing fitted curves based on the m ratio sets mentioned in this claim.

16. The method according to claim 8 wherein one or more of said first m ratio set, said second m ratio set, said third m ratio set or said fourth m ratio set calculated from said first assay conducted on a sample are compared to one or more of first m ratio set, second m ratio set, third m ratio set or fourth m ratio set calculated from said calibration dataset to estimate a probable range of concentration of said common analyte by comparing derivatives of fitted curves based on the m ratio sets mentioned in this claim.

17. The method according to claim 9 wherein for one or more of said first m ratio set, said second m ratio set, said third m ratio set or said fourth m ratio set calculated from said first assay conducted on a sample are compared to one or more of first m ratio set, second m ratio set, third m ratio set or fourth m ratio set from said additional calibration dataset to estimate a probable range of concentration of said common analyte by comparing derivatives of fitted curves based on the m ratio sets mentioned in this claim.

* * * * *

UNITED STATES PATENT AND TRADEMARK OFFICE
CERTIFICATE OF CORRECTION

PATENT NO. : 7,501,290 B2
APPLICATION NO. : 11/901117
DATED : March 10, 2009
INVENTOR(S) : Brian Hanley It is certified that error appears in the above-identified patent and that said Letters Patent is hereby corrected as shown below:

Col. 6, Line 9: The set of m is a composed of 4 ...
   Should be: The set of m is composed of 4 ...
Col. 7, Line 50: SMPCSs" defines on of the mean m values ...
   Should be: SMPCSs" defines one of the mean m values ...
Col. 11, Line 43: intraplex interpretation software based retrievable ...
   Should be: intraplex interpretation software retrievable ...
Col. 12, Line 49: IDGs, where in this case n=1 for each m SMPCS-IDGs is then
   Should be: IDGs, where in this case n=1 for each m SMPCS-IDG is then
Col. 13, Line 50: 003, or 00. Subset B could have SMPCS ...
   Should be: 003, or 004. Subset B could have SMPCS ...
Col. 14, Lines 27-32: In general, the principles of the invention and including such departures from the present disclosure as come within known or customary practice within the art to which the invention pertains as may be applied to the essential features hereinbefore set forth and as follows in the scope of the appended claims.
   Should be: In general, the principles of the invention and including such departures from the present disclosure as come within known or customary practice within the art to which the invention pertains as may be applied to the essential features hereinbefore are set forth as follows in the scope of the appended claims.

Signed and Sealed this

Twenty-sixth Day of May, 2009

JOHN DOLL
*Acting Director of the United States Patent and Trademark Office*